(12) United States Patent
Schoch

(10) Patent No.: US 8,585,883 B2
(45) Date of Patent: Nov. 19, 2013

(54) ISOTACHOPHORETIC ANALYTE EXTRACTION

(75) Inventor: Reto Schoch, Speicherschwendi (CH)

(73) Assignee: Swissfluidics AG, Gais (CH)

( * ) Notice: Subject to any disclaimer, the term of this patent is extended or adjusted under 35 U.S.C. 154(b) by 204 days.

(21) Appl. No.: 13/167,059

(22) Filed: Jun. 23, 2011

(65) Prior Publication Data

US 2011/0297546 A1 Dec. 8, 2011

(30) Foreign Application Priority Data

Jul. 6, 2010 (EP) .................................... 10168635

(51) Int. Cl.
*G01N 27/447* (2006.01)
*G01N 27/453* (2006.01)

(52) U.S. Cl.
USPC .......................................... 204/549; 204/645

(58) Field of Classification Search
USPC ................................................. 204/549, 645
See application file for complete search history.

(56) References Cited

U.S. PATENT DOCUMENTS

| | | | |
|---|---|---|---|
| 5,817,225 | A | 10/1998 | Hinton |
| 6,685,813 | B2 | 2/2004 | Williams et al. |
| 2002/0039751 | A1 | 4/2002 | Parce |
| 2002/0189946 | A1 | 12/2002 | Wainright et al. |
| 2006/0254915 | A1 | 11/2006 | Hirokawa et al. |
| 2008/0197019 | A1 | 8/2008 | Santiago |

FOREIGN PATENT DOCUMENTS

| | | |
|---|---|---|
| CA | 2667463 | 5/2008 |
| DE | 19927535 | 1/2001 |
| WO | WO2008/006201 | 1/2008 |
| WO | WO2008/053047 | 5/2008 |
| WO | WO2008/082876 | 7/2008 |
| WO | WO2009/079028 | 6/2009 |

OTHER PUBLICATIONS

Lin et al., Addressable Electric Fields for Size-Fractioned Sample Extraction in Microfluidic Devices, *Anal. Chem.* (2005) 77, 4338-4347.
Khurana et al., Preconcentration, Separation, and Indirect Detection of Nonfluorescent analytes Using Fluorescent Mobility Markers, *Anal. Chem.* (2008) 80, 279-286.
Hirokawa et al., Simulated Qualitative and Quantitative Indices of 287 Anionic Substances in the Rang pH 3-10, *Journal of Chromatograph*271, D1, (1983).

(Continued)

*Primary Examiner* — J. Christopher Ball
(74) *Attorney, Agent, or Firm* — Cozen O'Connor

(57) ABSTRACT

An isotachophoresis method for preconcentrating and isolating a plurality n of charged analytes ($A_i$, with i=1 to n) contained in a sample is disclosed, wherein each one of the analytes $A_i$ has an effective electrophoretic mobility $\mu_{Ai}$ obeying the fully ordered relationship $\mu_{A1} > \mu_{A2} >$ etc. $> \mu_{An}$, comprising the step of preparing a mixture of said sample and a number n−1 of spacer compounds ($S_k$, with k=1 to n−1) wherein each one of said spacer compounds ($S_k$) has an effective electrophoretic mobility $\mu_{Sk}$ obeying the fully ordered relationship $\mu_{Ak} > \mu_{Sk} > \mu_{Ak+1}$. An axial electric field is applied along the longitudinal axis of a separation channel, thereby causing a preconcentration and separation of the analytes and spacers forming respective focused spacer zones and focused analyte zones that flow along the longitudinal axis. Each one of the spacer compounds ($S_k$) has an initial concentration ($c_{0,Sk}$) selected in such manner as to substantially correspond, at its preconcentrated concentration ($c_{Sk}$) in the respective focused spacer zone, to a volume of the main separation channel enclosed between an associated pair of adjacent extraction channels ($E_k$) and ($E_{k+1}$). Through this spatial displacement of analytes $A_i$ by spacers $S_k$, the analytes can be selectively extracted into the extraction channels $E_i$.

10 Claims, 8 Drawing Sheets

(56) References Cited

OTHER PUBLICATIONS

Jaros et al., Eigenmobilities in background electrolytes for capillary zone electrophoresis: IV. Computer program PeakMaster, *Electrophoresis* (2004), 25, 3080-3085.

Khurana et al., Sample Zone Dynamics in Peak Mode Isotachophoresis, *Anal. Chem.* 80, 6300(2008).

Li et al., Design of a PMMA Chip for Selective Extraction of Size Fractioned DNA, Conference on Nan/Micro Engineered and Molecular Systems, Jan. 18-21, 2006 Zhuhai, China.

European Search Report dated Aug. 30, 2010.

ISOTACHOPHORETIC ANALYTE EXTRACTION

FIELD OF THE INVENTION

The present invention generally relates to the field of analytical electrophoresis systems and methods. More specifically, this invention focuses on highly selective isotachophoresis and electrokinetic transport for the extraction of charged molecules.

BACKGROUND OF THE INVENTION

In presently used centralized testing systems samples are taken and shipped to a central lab for analysis, e.g. in clinical diagnostics, life sciences, biodefense, food and water industries, and agricultural and environmental sensing. This leads to significant costs and long periods of time to result. In contrast, portable sample preparation devices can introduce a shift not only in the instrumentation but in the entire measurement procedure by performing measurements anytime and anywhere. Sample preparation is the limiting element for such devices, since this process is typically done manually, but it also has been automated by mechanizing manual processing methods through robotic systems. Commercially available instruments are thus large, expensive and complex with significant reagent and consumable usage.

Microfluidics offers reduced reagent use, increased specificity and robustness, integration and automation, potential for parallel analysis, cost-effective devices fabricated by injection molding, and controlled channel designs. Lab-on-a-chip devices are thus particularly interesting for portable sample preparation modules as well as for cost-effective and automated lab instruments.

For the transport and separation of charged molecules in capillaries and micro-channels, electrophoresis is often employed and has found widespread applications. However, the sensitivity and selectivity to accurately handle and separate substances in tubings is limited, thus requiring efficient sample preconcentration methods.

One approach to preconcentrate a sample is isotachophoresis (ITP), which allows simultaneous separation of several analytes. ITP uses an imposed electrophoretic mobility gradient to create concentrated analyte zones with nondispersing interfaces in an elongated channel. Analyte ions to be stacked and separated are typically introduced between a leading (LE) and a trailing electrolyte (TE) with an effective mobility respectively higher and lower than those of the analytes. Under the influence of an electric field, analyte ions redistribute themselves into sequential zones in order of reducing effective mobility (starting from LE to TE). After initial transients, ITP based separations typically result in adjacent, contiguous zones of analytes moving at identical speed downstream in the main separation channel.

For the separation of charged components, U.S. Pat. No. 6,685,813 of Williams is based on the titration of analytes. The method involves loading a microchannel with a sample, placed between a TE having a selected concentration of a titratable species, and an LE. When a voltage is applied over the microchannel, charged components stack by ITP, and electrolytic hydroxyl or hydrogen ions migrate into the TE, titrating the species therein which then overtake the charged sample components and thus separate by zone electrophoresis.

There are several patent applications on ITP based preconcentration of analytes combined with their separation by electrophoresis and analysis. US Patent Application Publication No. 2006/0254915 of Hirokawa describes a microchip electrophoresis method for sample preconcentration and separation in two individual steps. Sample concentration is performed by ITP, followed by separation using zone electrophoresis or gel electrophoresis. Similarly, US Patent Application Publication No. 2002/0189946 of Wainright and Williams is drawn to a simple two-electrode injection scheme with isotachophoretic stacking, followed by zone electrophoretic separation in the same channel. Further, US Patent Application Publication No. 2005/0133370 of Park et al. discloses methods and devices for spatially separating at least first and second components by means of a spacer, which components are stacked by ITP and injected in different channel segments for their separation by mobility therein.

More specifically, U.S. Pat. No. 5,817,225 by Hinton describes an electrophoretic unit for the purification, concentration and size fractionation of nucleic acids contaminated by organic acids using specific LE and TE chemistries. International patent application WO 2009/079028 A1 of Young also employs gels for the concentration of proteins and DNA using ITP. The method is drawn to simultaneously co-purify and concentrate nucleic acids and protein targets with positive and negative net charge into a single volume, which are initially placed in the middle of a gel such that ITP will run in two directions towards both a positive and negative electrode when a voltage is applied.

A method to directly detect analytes that are per se undetectable using directly detectable spacer compounds has been disclosed by Santiago under US Patent Application Publication No. 2008/0197019 A1. These charged molecules are concentrated and separated into zones using ITP, and a displacement between the zones of directly detectable spacer compounds is used to determine the presence of the analyte that is not directly detectable.

Two international patent applications disclose partially using ITP for the concentration and separation of molecules within their systems. WO 2008/082876 A1 of Balgley provides a method for performing off-line multi-dimensional separation and analysis of a sample, including the separation of the heterogeneous biomolecular sample into a plurality of fractions using a partial capillary ITP mechanism. WO 2008/053047 A2 of Weber focuses on a specific type of free-flow electrophoresis (FFE), free-flow ITP (FFITP), performed in an almost quadratic electrophoresis chamber to separate different analytes.

However, kits for the ITP based extraction of specific fractions from a complex sample using custom electrolytes and disposable modules, which can be integrated in portable or handheld devices or automated for cost-effective lab instruments have not been disclosed so far.

SUMMARY OF THE INVENTION

According to one aspect of the invention (claim 1), there is provided a method for preconcentrating and isolating a plurality n of charged analytes ($A_i$, with i=1 to n) contained in a sample by isotachophoresis, each one of said analytes $A_i$ having an effective electrophoretic mobility $\mu_{Ai}$, said effective electrophoretic mobilities $\mu_{Ai}$ obeying the fully ordered relationship $\mu_{A1} > \mu_{A2} >$ etc. $> \mu_{An}$, by means of an apparatus comprising:

a main separation channel (C) with a proximal end (P) and a distal end (D), means for loading a supplemented sample portion into an internal segment of said main separation channel located between said proximal end and said distal end, means for applying an electric field ($\hat{E}$) between said proximal end (P) and said distal end (D), a plurality n of extraction channels ($E_i$, with i=1 to n) being transversely oriented in respect of said main separation channel (C) and having respective junctions with said main separation channel located at different sites thereof, each extraction channel having an extraction part leading out of the main separation channel, means for detecting focused zones within said separation channel (C) and/or means for measuring a flow velocity along a longitudinal axis of said separation channel under the influence of an electric field ($\hat{E}$) applied along said axis by said means for applying an electric field, means for applying a transversal flow along each one of said extraction channels ($E_i$) for extracting any one of said analytes located at the respective junction of the extraction channel ($E_i$) and the main separation channel (C), said method comprising the steps of:

loading a leading electrolyte (LE) into a distal channel region adjacent said distal end and a trailing electrolyte (TE) into a proximal channel region adjacent said proximal end, said leading electrolyte (LE) having an effective electrophoretic mobility $\mu_{LE} > \mu_{A1}$ and said trailing electrolyte (TE) having an effective electrophoretic mobility $\mu_{TE} < \mu_{An}$, adding a supplemented sample to said proximal channel region (P), said supplemented sample comprising a mixture of said sample and a number n−1 of spacer compounds ($S_k$, with k=1 to n−1), each one of said spacer compounds ($S_k$) having an effective electrophoretic mobility $\mu_{Sk}$ said effective electrophoretic mobilities $\mu_{Sk}$ obeying the fully ordered relationship $\mu_{Ak} > \mu_{Sk} > \mu_{Ak+1}$, applying an axial electric field between said proximal end (P) and said distal end (D), thereby causing a preconcentration and separation of said analytes and spacers forming respective focused spacer zones and focused analyte zones that flow along said longitudinal axis, each one of said spacer compounds ($S_k$) in said supplemented sample having an initial concentration ($c_{0,Sk}$) selected in such manner as to substantially correspond, at its preconcentrated concentration ($c_{Sk}$) in the respective focused spacer zone, to a volume of said main separation channel enclosed between an associated pair of adjacent extraction channels ($E_k$) and ($E_{k+1}$), detecting the position and/or measuring the velocity of said focused zones, optionally stopping the process by switching off said electric field ($\hat{E}$) when the focused zone of each analyte ($A_i$) is located at the respective junction with the extraction channel ($E_i$), applying a transversal flow of the part of the supplemented sample located at the junction of the main separation channel and the respective extraction channel, thereby transferring each preconcentrated analyte ($A_i$) away from the main separation channel for said analyte isolation.

It will be understood that the volume of the main separation channel portion enclosed between an associated pair of adjacent extraction channels $E_k$ and $E_{k+1}$ is given by the length times the average cross section of said channel portion. In the preferred case of a main separation channel having a constant cross section, the volume will simply be given by the length times the cross section. In any case, there will generally be a known relation between the volume of a channel region and the length thereof.

If the analyte molecules are contained in cells, a lysing buffer may be added to the sample so as to release the analytes into solution for subsequent processing.

According to one embodiment, the addition of the supplemented sample to the proximal channel region is accomplished by loading the supplemented sample into a channel segment located between the leading electrolyte and the trailing electrolyte (claim 2).

According to another embodiment, the addition of the supplemented sample to the proximal channel region is accomplished by first preparing a mixture of the supplemented sample and the trailing electrolyte and then loading the mixture into the proximal channel region (claim 3).

As generally known in the field of isotachophoresis, there are several techniques for detecting the presence of an analyte. Depending on the analytes, this will preferably involve fluorescence detection or some kind of electrical detection. According to an advantageous embodiment (claim 4), the presence and optionally the instant concentration of an analyte ($A_i$) is detected electrically as a current or resistance plateau between:

two adjacent spacer compounds ($S_{i-1}$) and ($S_i$) for i=2 to n−1;

the leading electrolyte (LE) and adjacent spacer compound ($S_1$) for $A_1$;

adjacent spacer compound ($S_{n-1}$) and the trailing electrolyte (TE) for $A_n$.

There are several ways of collecting the analytes after they have been separated by isotachophoresis. According to one embodiment, the step of applying a transversal flow is carried out until each analyte ($A_i$) has reached a collection zone located at an end of the extraction part of the respective extraction channel ($E_i$) (claim 5). According to another embodiment, the step of applying a transversal flow is interrupted when each analyte has accumulated in a zone of the respective extraction channel ($E_i$) displaced from the main separation channel (C), followed by a step of reapplying the electric field ($\hat{E}$) and thus causing any residual analyte present in the main separation channel (C) to be removed therefrom towards the distal end (D), followed by switching off the electric field ($\hat{E}$) and reapplying the transversal flow until each analyte ($A_i$) has reached a collection zone located at the distal end of the extraction part of the respective extraction channel ($E_i$) (claim 6). In addition, the analytes can be extracted into an extraction buffer (EB) that is different from the leading electrolyte (LE).

In many applications it will be preferable that the leading electrolyte (LE) and the trailing electrolyte (TE) have substantially the same pH value; moreover, depending on the type of analytes, the leading and trailing electrolyte may be provided with a sieving matrix and/or an agent for electroosmotic flow suppression (claim 7).

It will be understood that there are several methods for determining effective electrophoretic mobilities. According to one embodiment, wherein the effective electrophoretic mobility ($\mu_{Ai}$) of a given analyte ($A_i$) is determined by means of isotachophoresis or electrophoresis (claim 8).

According to a preferred embodiment (claim 9), the step of selecting the initial concentration ($c_{0,Sk}$) of each one of said spacer compounds ($S_k$) is carried out iteratively and comprises the steps of:

a) providing a mixture of said spacer compounds ($S_k$) with respective startup initial concentrations ($C'_{0,Sk}$), b) starting an isotachophoretic process with said mixture, thereby causing a separation and preconcentration of said spacer zones flowing along said longitudinal axis, c) determining the associated length ($d_{Sk}$) of each spacer zone,
d) determining a deviation measure ($m_k$) for each one of said lengths ($d_{Sk}$) versus the distance ($d_{Ek}$) between the associated pair of adjacent extraction channels ($E_k$) and ($E_{k+1}$),
e) using said deviation measures ($m_k$) to calculate a set of refined initial concentrations ($c''_{0,Sk}{}^{(r)}$),
f) repeating steps a) to e) using said refined initial concentrations ($c''_{0,Sk}{}^{(r)}$) instead of said startup initial concentrations ($c'_{0,Sk}$) until none of said deviation measures ($m_k$) exceeds a predefined tolerance threshold,
g) using said refined initial concentrations ($c''_{0,Sk}{}^{(r)}$) as the initial concentrations ($c_{0,Sk}$) for preparing said supplemented sample.

In principle, the above defined method of selecting the initial concentration ($c_{0,Sk}$) of each one of said spacer compounds ($S_k$) may be carried out with a mixture of spacer compounds that does not contain any analytes. However, in many cases it will be advantageous to add the charged analytes ($A_i$) to the mixture of spacer compounds so as to detect the separation zone between two spacer compounds via a signal of the analyte that accumulates therein. In particular, the step of determining the associated length ($d_{Sk}$) of each spacer zone may be carried out by detecting focused analyte zones separating said focused spacer zones, e.g. via fluorescence detection of said analytes (claim 10).

According to another aspect of the invention, there is provided an apparatus for preconcentrating and isolating a plurality n of charged analytes ($A_i$, with i=1 to n) contained in a sample by isotachophoresis, each one of said analytes ($A_i$) having an effective electrophoretic mobility $\mu_{Ai}$, said effective electrophoretic mobilities $\mu_{Ai}$ obeying the fully ordered relationship $\mu_{A1} > \mu_{A2} >$ etc. $> \mu_{An}$, said apparatus comprising:

a main separation channel (C) with a proximal end (P) and a distal end (D),
means for adding a supplemented sample into an internal segment of said main separation channel located between said proximal end (P) and said distal end (D),
means for applying an electric field (E) between said proximal end (P) and said distal end (D),
a plurality n of extraction channels ($E_i$, with i=1 to n) being transversely oriented in respect of said main separation channel (C) and having respective junctions with said main separation channel located at different sites thereof, each extraction channel having an extraction part leading out of the main separation channel,
means for detecting focused spacer zones and focused analyte zones within said separation channel (C) and/or means for measuring a flow velocity along a longitudinal axis of said separation channel under the influence of an electric field applied by said means for applying an electric field,
means for applying a flow along each one of said extraction channels for extracting any one of said analytes located at the respective junction of the extraction channel (C) and the main separation channel,
a leading electrolyte (LE) contained in a distal channel region adjacent said distal end and a trailing electrolyte (TE) contained in a proximal channel region adjacent said proximal end, said leading electrolyte (LE) having an effective electrophoretic mobility $\mu_{LE} > \mu_{A1}$ and said trailing electrolyte (TE) having an effective electrophoretic mobility $\mu_{TE} < \mu_{An}$,
a supplemented sample contained in said proximal channel region (P),
said supplemented sample comprising a mixture of said sample and a number n−1 of spacer compounds ($S_k$, with k=1 to n−1), each one of said spacer compounds ($S_k$) having an effective electrophoretic mobility $\mu_{Sk}$, said effective electrophoretic mobilities $\mu_{Sk}$ obeying the fully ordered relationship $\mu_{Ak} > \mu_{Sk} > \mu_{Ak+1}$,
each one of said spacer compounds ($S_k$) in said supplemented sample having an initial concentration ($c_{0,Sk}$) selected in such manner as to substantially correspond, at its preconcentrated concentration ($c_{Sk}$) in the respective focused spacer zone, to a volume of said main separation channel enclosed between an associated pair of adjacent extraction channels ($E_k$) and ($E_{k+1}$).

In one embodiment of the apparatus, each extraction channel ($E_i$) comprises a collection zone located at an end of the extraction part thereof. In particular, the collection zone may be configured as a reservoir, as a droplet forming at the end of an extraction channel, or as an injection channel leading into an additional main separation channel where the analytes are preconcentrated and isolated further.

In a further embodiment, each extraction channel ($E_i$) further comprises an injection part leading into the main separation channel. Preferably, such an injection part will have a cross section that is smaller than a cross section of the corresponding extraction part. Moreover, said injection and/or extraction parts may be provided with a constriction in a region adjacent or at said main separation channel (C). If analytes have to be extracted into a different buffer than the leading electrolyte (LE) for subsequent analysis, the apparatus may further comprise a plurality of extraction buffer sections (EB), each one having a channel leading into the junction of an extraction part or injection part of the extraction channel and the main separation channel.

According to an advantageous embodiment, the means for detecting focused zones comprise electrodes arranged in the main separation channel (C) and/or in the extraction channels ($E_i$) and/or in the collection zones.

The present invention provides systems and methods for robust and repeatable extractions of at least one specific analyte (typically being low-abundant) from a complex sample. The analytes are separated at a given distance from each other using spacer compounds, and these charged species are focused by ITP in a microchannel between a leading and a trailing electrolyte which can contain a sieving matrix to increase separation resolution. The preconcentrated and self-focused ITP zones travel downstream, and once they arrive at their predetermined site as being continuously controlled, they are all simultaneously transferred into extraction channels by an applied fluid flow perpendicular to the main separation channel. The analytes are dispensed into reservoirs, droplets are generated for their detailed analysis, or they are reinjected into an additional main separation channel where the analytes are preconcentrated and isolated further to achieve increased extraction purities.

The present methods allow the realization of miniaturized, portable, and automated sample preparation modules, which can be integrated in instruments for point-of-care diagnostics, life science, biodefense, food and water industries, and agricultural and environmental sensing. In addition, these instruments can be manufactured cost-effectively, being of interest to the drug discovery industry and R&D labs working with 2D gel electrophoresis. For such application fields, these methods are designed for the fractionation of samples into distinct zones, allowing the separation of proteins from nucleic acids, the fractionation of proteins by size or charge, or the fractionation of nucleic acids by length, for example.

The methods, apparatus and required electrolytes can be provided as a kit for carrying out separation; preconcentration and isolation of analytes, wherein the apparatus includes disposable or semi-disposable microfluidic devices with integrated channels. For dispatching purposes, these channels can be dry, prefilled with custom electrolytes at the final concentration or as a concentrated stock solution, or the electrolytes can be present in a lyophilized form. The electrolytes can be provided as prefilled amounts for one or multiple measurements. This allows the user to perform measurements on the field, in the lab or anywhere else by adding the required amount of custom electrolytes or water.

Before the ITP focusing and extraction process is initiated, in one embodiment, the sample is introduced into the main separation channel between the proximal channel region and distal channel region through specific injection channels. In another embodiment, the proximal end of the main separation channel is filled with TE, sample and spacers before the electric field is applied, allowing a continuous injection of sample and spacers during the ITP process.

In the first step the electric field is applied along the main separation channel, resulting in the bracketing of each analyte by two predefined spacers, one upstream and one downstream, except for the first and last analyte which can be bracketed by one spacer and the LE and TE, respectively. The analytes and spacers can be selected according to the protocol provided in the detailed description of this invention, such that they are preconcentrated and separated in alternating and adjacent zones according to the ITP mechanism. The electrolytes can contain a sieving matrix which increases the separation resolution and prevents bubbles and big particles of entering into the channels, and/or a porous membrane can be integrated into the reservoirs and/or channels for filtration purposes. Further, an agent for electro-osmotic flow suppression is typically added to the electrolytes to increase the dominance of the electrophoretic transport.

The electrolyte chemistry of the spacers are conceived such that the composition, ionic strength, and pH value lead to plateau mode ITP with predefined lengths of the plateaus. In contrast, the analytes are typically focused in peak mode ITP because they are present at lower concentrations (typically low-abundant), although they can also reach plateau zones.

Due to the known plateau lengths of the spacers (EQ. 5) the distance between the individual analytes is set, and these distances correspond to the inter-channel spacings of the extraction channels. Thus, the ITP focused analyte zones will be just opposite of their corresponding extraction channel once the ITP electric field is switched off. The precise placement of the ITP zones in front of their corresponding extraction channels is controlled by the detection of the focused zones.

In the second step, an electrokinetic or pressure-driven flow is applied along the extraction channels, crossing the main separation channel, and therefore injecting the focused analytes into the corresponding extraction channels only. This transfer process is only applied briefly until the analyte zones are inside the extraction channels. The extraction purity and yield can be increased by optimizing the widths of the extraction channels at the cross, or integrating shaping electrodes or constrictions to optimize the electric field or flow lines, as described by Lin et al. (*Anal. Chem.*, 2005, 77, 4338).

Then, the electric field along the main separation channel is reapplied to transport the remaining charged molecules in this channel to the waste reservoir. Subsequently, the fluid flow through the extraction channels is reinitiated to transport the analyte molecules into the extraction reservoirs which are located at the end of the channels. Instead of transporting the analytes into the reservoirs, droplets can be generated by continuously dispensing the liquid on a surface which is located at the chip interface. Further, the analytes can be reinjected into an additional main separation channel where the analytes are preconcentrated and isolated further to achieve increased extraction purities.

BRIEF DESCRIPTION OF THE DRAWINGS

The above mentioned and other features and objects of this invention and the manner of achieving them will become more apparent and this invention itself will be better understood by reference to the following description of various embodiments of this invention taken in conjunction with the accompanying drawings, wherein:

FIG. 5C shows a close-up of the area indicated by the dotted line in FIG. 5B.

DETAILED DESCRIPTION OF THE INVENTION

The present invention describes systems and methods to extract analytes (typically being low-abundant) of complex sample mixtures for automated lab instruments and handheld devices. It employs ITP based stacking using spacers, which are specifically engineered to match the extraction channel geometry, allowing robust and simultaneous extraction of several analytes. The extraction yield and purity can be optimized by an accurate timing of the extraction step and by an optimized design of the geometry of the microchannel crossings. After extraction of the analytes they can be transported into extraction reservoirs, directly dispensed into droplets for their subsequent analysis, or reinjected into an additional main separation channel where the analytes are preconcentrated and isolated further to achieve increased extraction purities.

Methods and systems of this invention can be used in several fields such as point-of-care diagnostics, life science, biodefense, food and water industries, and agricultural and environmental sensing. Analytes to be extracted can be, e.g., charged molecules such as amino acids, peptides, proteins, glycoproteins, biomarkers, hormones, metabolites, organelles, membranes, liposomes, lipids, saccharides and derivatives thereof, antibodies, antibody complexes, nucleic acids, nucleic acid—protein complexes, food additives, pathogens, viruses, drugs, heavy metals, toxins, toxic industrial chemicals, explosives, chemical weapons, biological weapons, ions, and/or the like. The sample containing the analytes can be a clinical sample derived from a body fluid or tissue sample, or it can be from an environmental source, for example. Further, the analyte to be extracted can be in agreement with immunoassay, protein sequencing, mass spectrometry, gels, PCR, isothermal amplification, hybridization reactions, microarrays, protein-DNA binding. The sample can be treated with a lysing buffer if the analyte molecules are contained in cells. This will release the analytes into solution for subsequent processing.

Figure 1A:
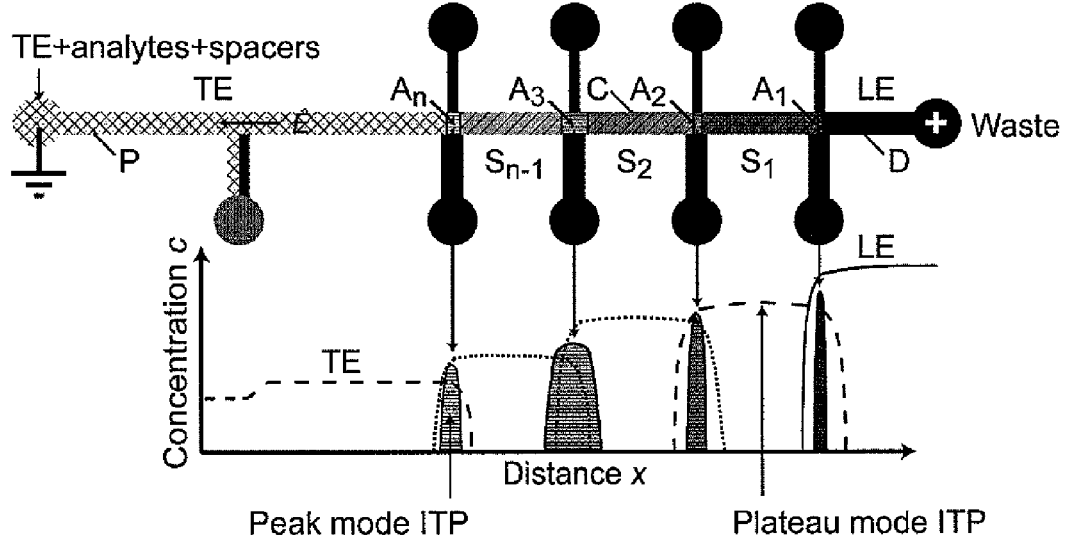
FIG. 1A is a schematic diagram of an exemplary microfluidic chip, showing the concentrations of the electrolytes during ITP focusing, not drawn to scale.
Figure 1B:
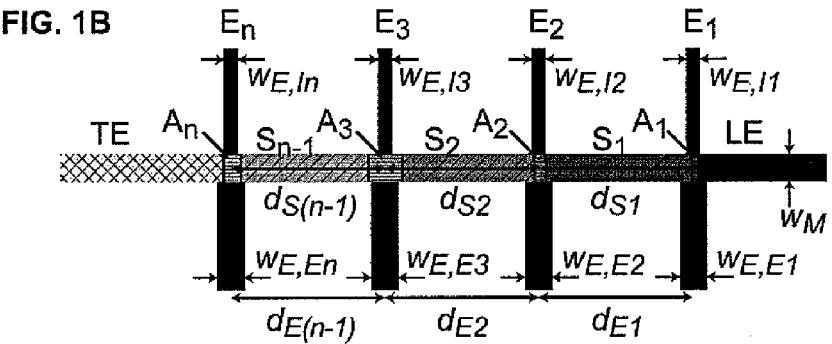
FIG. 1B shows the nomenclature of the channel dimensions, where $d_{Sk}$ is equal to $d_{Ek}$.
Figure 2A:
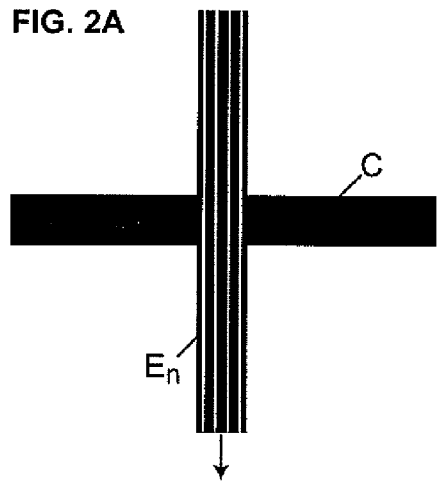
FIGS. 2A to E are schematic diagrams of the channel crossings, geometrically structured to achieve an optimal distribution of the electric field or flow lines across the main separation channel.
Figure 2B:
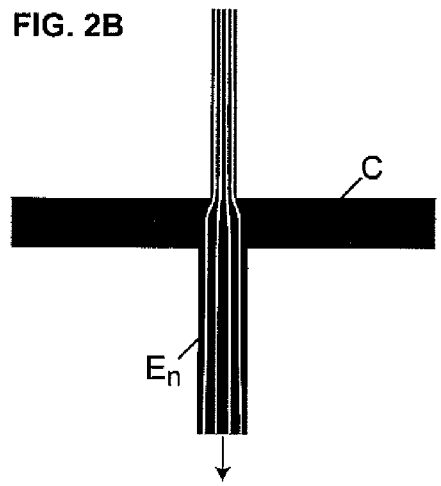
Figure 2C:
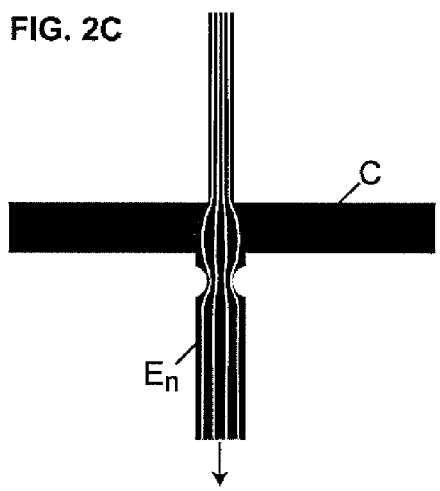
Figure 2D:
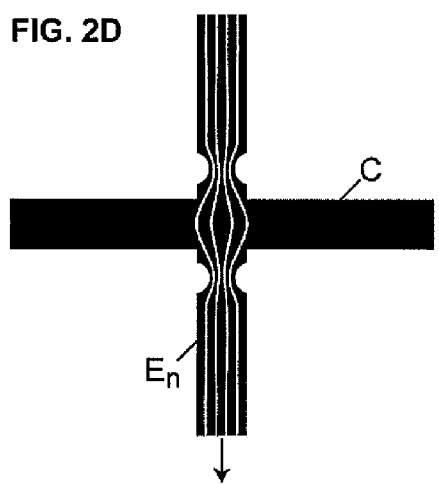
Figure 2E:
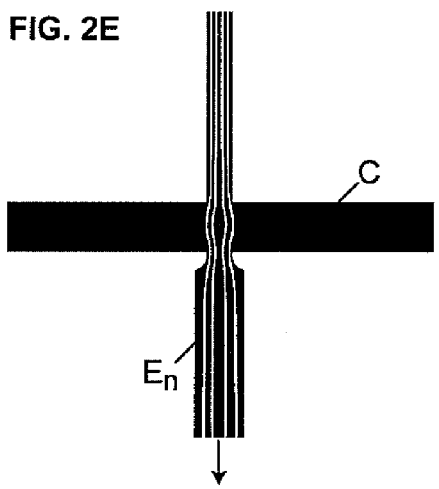

The ITP assay is designed to stack several analytes, at least one, in specific zones which are separated from each other by spacer molecules. FIG. 1A illustrates the ITP process, during which analytes ($A_1$ to $A_n$) and spacers ($S_1$ to $S_{n-1}$) redistribute themselves in sequential zones according to their effective electrophoretic mobility. This process obeys the Kohlrausch regulating function (KRF), $$KRF(x) = \sum \frac{|z_j|c_j(x,t)}{\mu_j}, \tag{1}$$

where z is the ion valence of specie j, c is the concentration of specie j, x is the position in the main separation channel, t is the time, and $\mu$ the effective electrophoretic mobility of specie j. The effective electrophoretic mobility is defined as:

$$\mu = \frac{v}{\hat{E}}, \tag{2}$$

where v is the average observable velocity and $\hat{E}$ the electric field at the specific experimental conditions. The effective electrophoretic mobility is different than the fully ionized electrophoretic mobility being more thought of as a material property. This results in a stepwise decrease of the concentrations of the analyte and spacer ions (starting from LE to TE). The spacers are engineered to reach plateau mode ITP, and the length of the plateau under ITP conditions $d_{Sk}$ corresponds within ±20% to the inter-channel separation distance $d_{Ek}$ as shown in FIG. 1B, thus:

$$d_{Ek} = d_{Sk}(\pm 20\%). \tag{3}$$

The preconcentrated concentration of spacer $S_k$ focusing in plateau mode ITP can be calculated with EQ. (1) and the electroneutrality condition (Khurana and Santiago, *Anal. Chem.*, 2008, 80, 279):

$$c_{Sk} = c_{LE}\left(\frac{\mu_{Sk}}{\mu_{LE}}\right)\left(\frac{\mu_{LE}+\mu_G}{\mu_{Sk}+\mu_G}\right), \tag{4}$$

where G is the common counterion. Under steady KRF conditions and a constant main separation channel cross section, the plateau length of each spacer zone depends on the injected plug length $d_{in}$ (FIG. 3A):

$$d_{Sk} = \frac{c_{0,Sk}d_{In}}{c_{Sk}} = \left(\frac{\mu_{LE}}{\mu_{Sk}}\right)\left(\frac{\mu_{Sk}+\mu_G}{\mu_{LE}+\mu_G}\right)\frac{c_{0,Sk}d_{In}}{c_{LE}}, \tag{5}$$

where $c_{0,Sk}$ is the initial concentration of spacer $S_k$. Therewith, the plateau length of each spacer zone can be calculated according to EQ. (5) as a function of the initial spacer concentration $c_{0,Sk}$. For the continuous injection scheme (FIG. 4) as described below, the injection length can be approximated as:

$$d_{In} = \mu_{Sk}\hat{E}t_{ITP}, \tag{6}$$

where $t_{ITP}$ is the time during which isotachophoretic focusing is performed.

Plateau mode ITP is reached when the charged molecules are present at sufficiently high initial concentration to form focused zones with a plateau (locally uniform) concentration profile at steady state. Differently, for low initial concentrations (and short focusing times) of charged molecules the zone width can be on the order or the interface width. This regime of ITP has been called the peak mode, where concentration profiles of the focused zones are approximately Gaussian rather than plateau shaped, see FIG. 1A. The interface width in peak mode ITP is governed by the electric field gradient and dispersion at the leading-trailing boundary.

In this ITP invention the spacers are designed to reach plateau mode, and analyte molecules are typically present at lower concentrations forming focused peaks. The separation distances between the analyte peaks is therefore mainly determined by the concentration of the spacers which separate analytes at a defined distance from each other, and the plateau length can be between 20 μm and 50 mm. Typical concentrations are as follow: mM range for LE and TE, μM for spacers, and nM or below for analyte molecules.

For the selection of the LE, TE and spacers their effective electrophoretic mobility is most important as it describes their order of focusing during ITP. The effective electrophoretic mobility of an ion changes with its $pK_a$ values, and is further dependent on a number of parameters such as buffer pH, ionic strength, ion type, ion valence and sieving matrix. The effective electrophoretic mobility of hundreds of anionic substances has been simulated by Hirokawa et al. (*J. Chrom.*, 1983, 271, D1). These results are included in the database of the freeware Peakmaster of Jaros at al. (*Electrophoresis*, 2004, 25, 3080), which is hereby incorporated by reference in its entirety.

A general procedure for the selection of the electrolytes and spacers is described in the following paragraphs. The effective mobility difference between the LE and TE should be as large as possible, between 10 to $70 \times 10^{-9}$ m$^2$ V$^{-1}$ s$^{-1}$, which allows running the ITP assay sufficiently fast (a few minutes) at approximately 10 to 500 V cm$^{-1}$. The effective mobility difference between the LE and TE further depends on the number of analytes which have to be extracted, since an effective mobility difference of at least 2 to $5 \times 10^{-9}$ m$^2$ V$^{-1}$ s$^{-1}$ between two plateau zones has be considered to achieve a sharply focused analyte peak. Thus, an ITP assay for the extraction of six analytes should be designed with a minimal effective mobility difference between the LE and TE of approximately 18 to $30 \times 10^{-9}$ m$^2$ V$^{-1}$ s$^{-1}$.

Next, the pH of the buffer system has to be determined at which the extraction will be performed, and the isoelectric points (pI) of the analyte molecules have to be considered for this step. The buffer pH value of the LE and TE is selected such that all analyte molecules are either negatively or positively charged, typically having a pH value between 3 and 10. Further, the selection of the buffer pH value allows the specific exclusion of contaminating molecules from migration if they are oppositely charged than the analyte molecules, and/or the pH value and sieving matrix composition and concentration can be chosen such that contaminating molecules and analyte molecules have different effective electrophoretic mobilities. The LE and TE do not have to have the same pH value, but it is recommended for simplicity. The second important parameter for the determination of an ITP electrolyte is its ionic strength. Khurana and Santiago (*Anal. Chem.*, 2008, 80, 6300), which is hereby incorporated by reference in its entirety, have described that optimal peak mode focusing is achieved if the LE has a conductivity of 0.8 S m$^{-1}$ and the TE 0.03 S m$^{-1}$.

So far, the pH and ionic strength of the electrolytes have been determined and their chemical compositions have to be set now, for which process the freeware Peakmaster is recommended. An acid and base can be chosen from Peakmaster's database and added to the background electrolyte constituent list of the program, for which components its system parameters can be calculated such as resulting pH, ionic strength, conductivity and buffer capacity. The concentrations of the acid and base can be changed until the desired system parameters are obtained for the LE and TE. Since 0.8 S m$^{-1}$ and 0.03 S m$^{-1}$ are optimal ionic strengths for the LE and TE as described above, the final concentrations will be around 100 mM and approximately 10 mM, respectively.

The effective electrophoretic mobility of the analytes can potentially be found in the literature, but for the accurate design of the ITP assay the effective mobility of each analyte has to be determined experimentally. This can be performed with diverse experiments, out of which two are described here. The first one is an electrophoretic method, in which the analyte and a reference molecule with a precisely known effective electrophoretic mobility are injected into a separation channel over which an electric field is applied. For calibration purposes, both molecules are fluorescently labeled such that they can be investigated with a fluorescence microscope. After injection the two molecules will separate according to their effective mobility, and since the effective mobility of the reference molecule is known, the one of the analyte can be readily calculated.

The second method for the determination of the effective electrophoretic mobility of an analyte is based on ITP. In the first iteration experiment, ITP is performed with the LE, TE (as determined above) and the analyte, and it is verified that the analyte molecule is focusing between the LE and TE. For calibration purposes, the analyte molecule can be fluorescently labeled for optical detection. Then, the TE is replaced with another TE having a higher effective mobility by the selection of another ion from Peakmaster's database, or by changing the pH value of the TE to fine-tune its effective electrophoretic mobility, and the experiment is repeated. If the analyte is focusing, the effective mobility of the TE is still too low and it has to be increased again. Once the analyte is no longer preconcentrated, it can be concluded that the effective electrophoretic mobility of the analyte has to be between this TE and the previous TE. The smaller the TE mobility increments, the more accurate the determination of the analyte effective electrophoretic mobility.

Finally, the spacer molecules are added in Peakmaster to the TE at low concentrations, typically µM to mM, according to EQ. (5). First, spacer 1 with an effective electrophoretic mobility between analyte 1 and 2 (verified by the Peakmaster calculation function) is added to the constituent list. Then, spacer 2 can be added having an effective mobility between analyte 2 and 3, spacer 3 has to have an effective mobility between analyte 3 and 4, and so on. It has to be controlled after each iteration that the system parameters of the TE are still met.

Once the LE, TE and spacer molecules have been determined, it has to be verified experimentally that they indeed have the expected effective mobility and focusing order. Mobility shifts might occur if a sieving matrix is used, since the sieving matrix has not been considered during the simulation process with Peakmaster. In general, a sieving matrix is advantageous if two analytes have almost the same effective electrophoretic mobility in free solution but are different in size, allowing to increase their effective electrophoretic mobility difference by a size-exclusion mechanism through an optimization of the sieving matrix composition and concentration. The sieving matrix can be polysaccharides such as hydroxypropyl-, hydroxyethyl-, (hydroxypropyl)methyl-cellulose, an agarose gel, or a polymer such as a block copolymer (containing repeating oligomers of two or more different polymers), a linear polymer, a branched polymer or a cross-linked polymer.

An agent for the suppression of electro-osmotic flow is typically added to the electrolytes, allowing highest performance since the electrophoretic transport gets more dominant. Agents for electro-osmotic flow suppression can be selected from the group consisting of polyvinylpyrrolidones, polyethyleneglycols, polyethyleneoxides, polylactams, substituted polyacrylamide derivatives, water soluble methylhydroxyethyl derivatives of cellulose and polyvinylalcohol.

The effective electrophoretic mobility of the LE, TE and spacers have been verified experimentally, and the concentration of the spacer molecules has to be adjusted now. EQ. (5) has been used for a first approximation of the required spacer concentration, and this parameter has to be fine tuned experimentally. This can be done through fluorescent calibration measurements, for example: the separation distance between two fluorescent analytes corresponds to the plateau length ($d_{Sk}$) of spacer compound ($S_k$), which parameter is adjusted through an in- or decrease of the initial spacer concentration $C_{0,Sk}$ until $d_{Ek}=d_{Sk}$ is met.

The channels can be fabricated in glass, plastic (particularly organic or condensation polymers), resins (such as PDMS—polydimethylsiloxane), silicon, or other materials can be employed as well. For glass, microfabrication technologies can be used for the structuring of the channels, whereas injection molding or precision milling are typically used for plastic materials.

Due to the fabrication process of the channels in glass using wet etching, the width w of all channels is typically bigger than their height h: w>h. The height is typically smaller than ~400 µm, and the width smaller than ~1 mm. In contrast, if different fabrication methods are employed the height can be equal to or even bigger than the width, reaching up to ~1 mm. For robust and repeatable extraction procedures, the plateau length of the spacers $d_{Sk}$ is longer than two times the width of the main separation channel $w_M$:

$$d_{Sk} > 2w_M \qquad (7)$$

The geometry of the ITP-extraction channel crossings is optimized to achieve highest extraction purities and yields. As shown in FIG. 1B, the injection and extraction parts of the extraction channels can be designed with different widths, $w_{E,Ji}$ and $w_{E,Ei}$, respectively. Further, potential geometries of the crossings are shown in FIG. 2A-E, where the lines represent electric field lines or flow lines for electrokinetic or pressure-driven flow, respectively. Introducing constrictions to the extraction channels just before, at and/or after the cross leads to optimized field/flow lines over the main separation channel, resulting in higher extraction purities and yields.

Figure 3A:
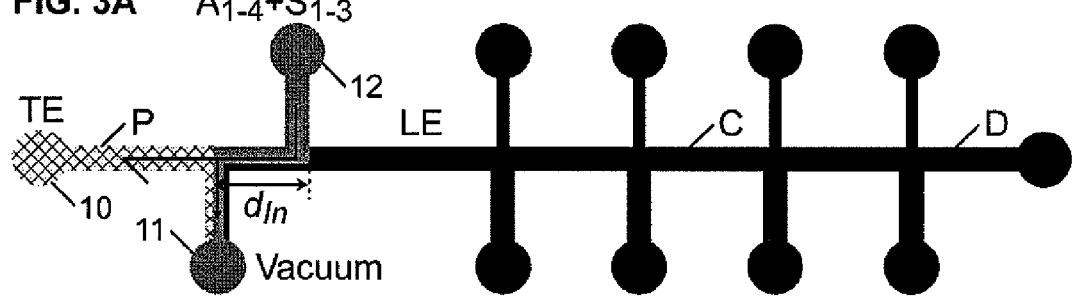
FIGS. 3A to C are schematic illustrations of the steps for isotachophoretic stacking for the case n=4, wherein the sample is introduced into the main separation channel in FIG. 3A, followed by the extraction of the analytes into the corresponding extraction channels.
Figure 3B:
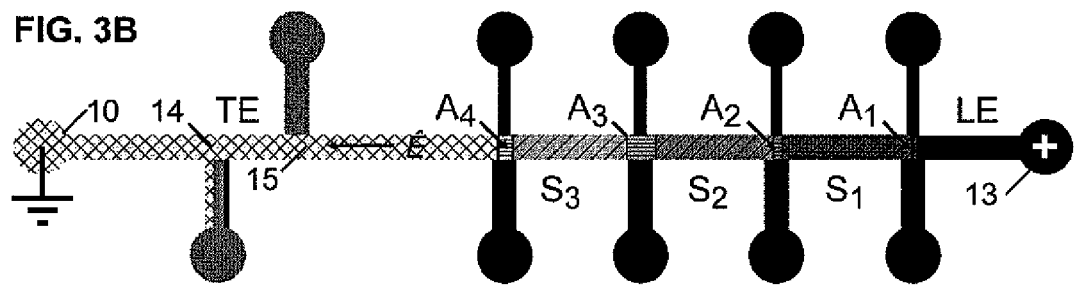
Figure 3C:
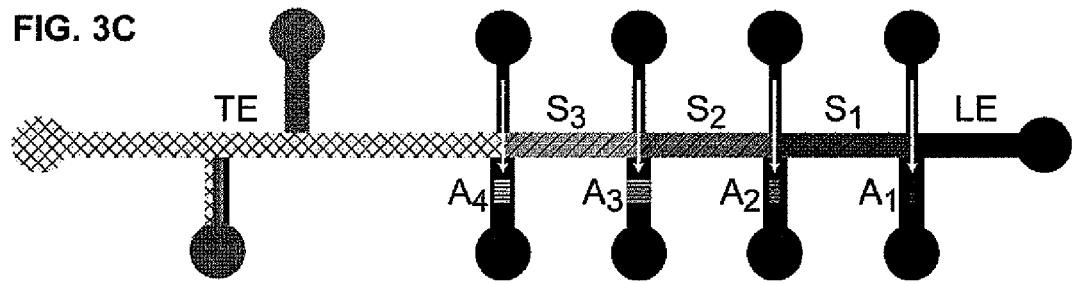
Figure 4A:
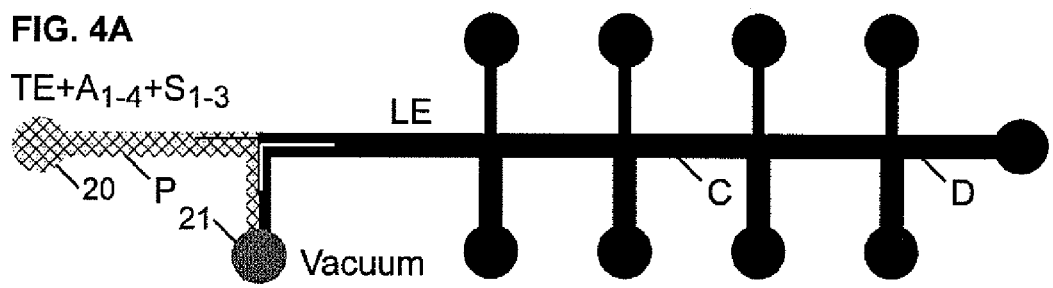
FIGS. 4A to C are schematic illustrations of the steps for isotachophoretic stacking for the case n=4, wherein the sample is continuously injected from the TE reservoir, followed by the extraction of the analytes into the corresponding extraction channels.
Figure 4B:
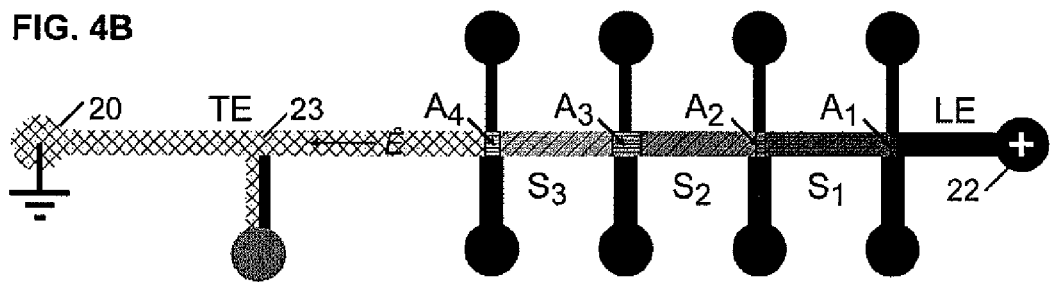

Focusing and extraction of analytes can be performed with many protocols, out of which two exemplary ones in accordance with the invention are shown in FIG. 3 and FIG. 4. In FIG. 3A, reservoir 10 is filled with TE, reservoir 12 with the sample containing analytes and spacers, and all the remaining reservoirs with LE which can contain a sieving matrix. Then, a vacuum is applied at reservoir 11 to fill the channels as shown. Next, an electric field on the order of 10 to 500 V cm$^{-1}$ is applied along the main separation channel between reservoirs 10 and 13, such that analyte and spacer molecules stack between the LE and TE as shown in FIG. 3B. Immediately after the application of the electric field, the stacked zones are between location 14 and 15, and then travel downstream until they are opposite of their corresponding extraction channels. Finally, the analyte zones are transferred into the extraction channels by either electrokinetic or pressure-driven flow, as shown in FIG. 3C by the arrows.

The sieving matrix has mainly two functionalities: (1) It increases the difference in the effective electrophoretic mobilities between the analytes of interest. The separation is purely based on the electrophoretic mobility if the electrolytes do not contain a sieving matrix, whereas a sieving matrix leads to a size-exclusion mechanism. (2) It prevents that bubbles and big particles are entering the channels, therewith increasing the robustness of the method. Further, a porous membrane can be integrated into the reservoirs or the channels for filtration of the sample and electrolytes, wherein the pores can be nano- or micrometer sized.

Figure 4C:
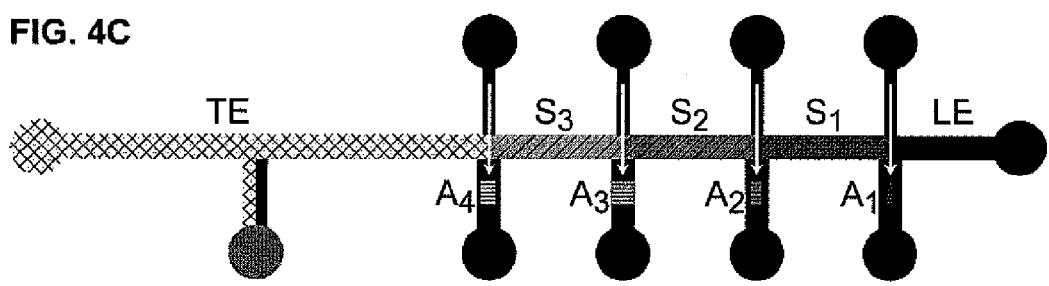

Another exemplary protocol for the stacking and extraction of analytes is shown in FIG. 4, where reservoir 20 is first filled with TE containing the analytes and spacers. All the other reservoirs except 21 are filled with LE which can contain a sieving matrix, and a vacuum is applied to reservoir 21, resulting in the filling of the channels as shown in FIG. 4A. In the next step, the ITP electric field of approximately 10 to 500 V cm$^{-1}$ is applied between reservoirs 20 and 22, leading to an instantaneous sample stacking near location 23. These zones travel downstream, are stopped once they are opposite to their corresponding extraction channels, and are extracted into these channels using either electrokinetic or pressure-driven flow as shown in FIG. 4C by the arrows.

Figure 5A:
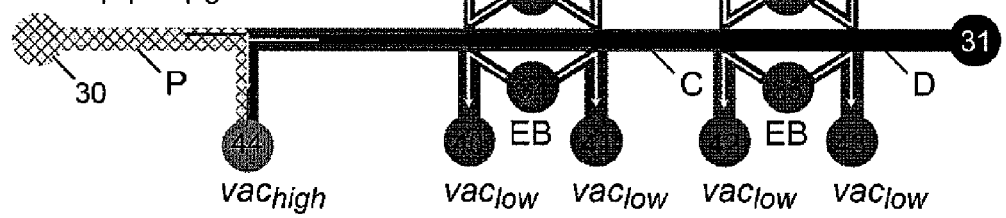
FIGS. 5A to C is a protocol for the extraction of analytes into custom extraction buffers (EB) for the case n=4; in the first step (FIG. 5A), high and low vacuums are applied to fill the extraction channels with the corresponding buffers, and then an electrokinetic flow is used in FIG. 5B to fill the main separation channel entirely with LE.
Figure 5B:
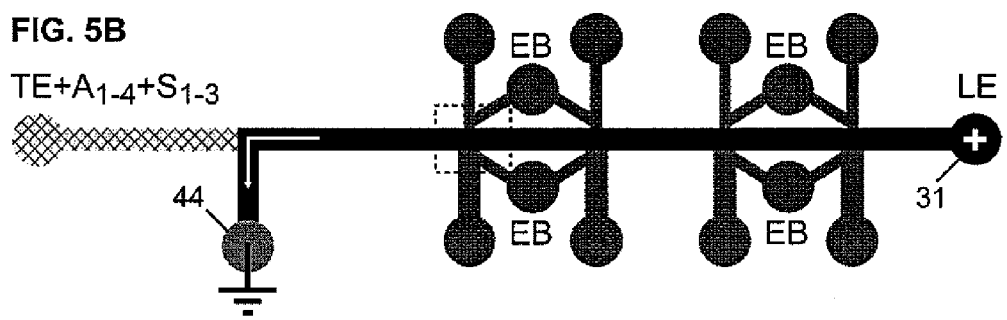
Figure 5C:
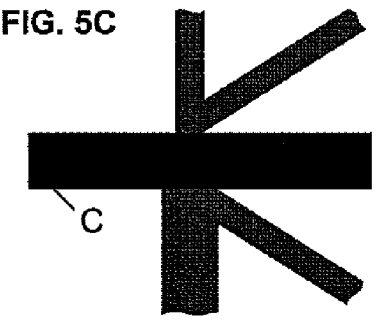

If analytes have to be extracted into a different buffer than the LE for subsequent analysis, a microchannel filling procedure can be applied as demonstrated in FIG. 5. The microchannel network of FIG. 4 is used in FIG. 5, but the same scheme can also be applied to the device of FIG. 3. First, reservoirs 32 to 35 are filled with the desired extraction buffer (EB), reservoir 31 with LE, and reservoir 30 with TE containing analytes and spacers. Then, a low vacuum is applied to reservoirs 36 to 43, and a high vacuum to reservoir 44. This allows filling the extraction channels with extraction buffer as shown by the white arrows in FIG. 5A, and a small amount of the extraction buffer is transported in the main separation channel into reservoir 44. To overcome this inhomogeneous filling of the main separation channel, an electrokinetic flow is applied in FIG. 5B from reservoir 31 to reservoir 44, such that the entire main separation channel is getting filled with LE only. FIG. 5C shows a close-up of the junction as indicated by the dotted line in FIG. 5B.

Figure 6:
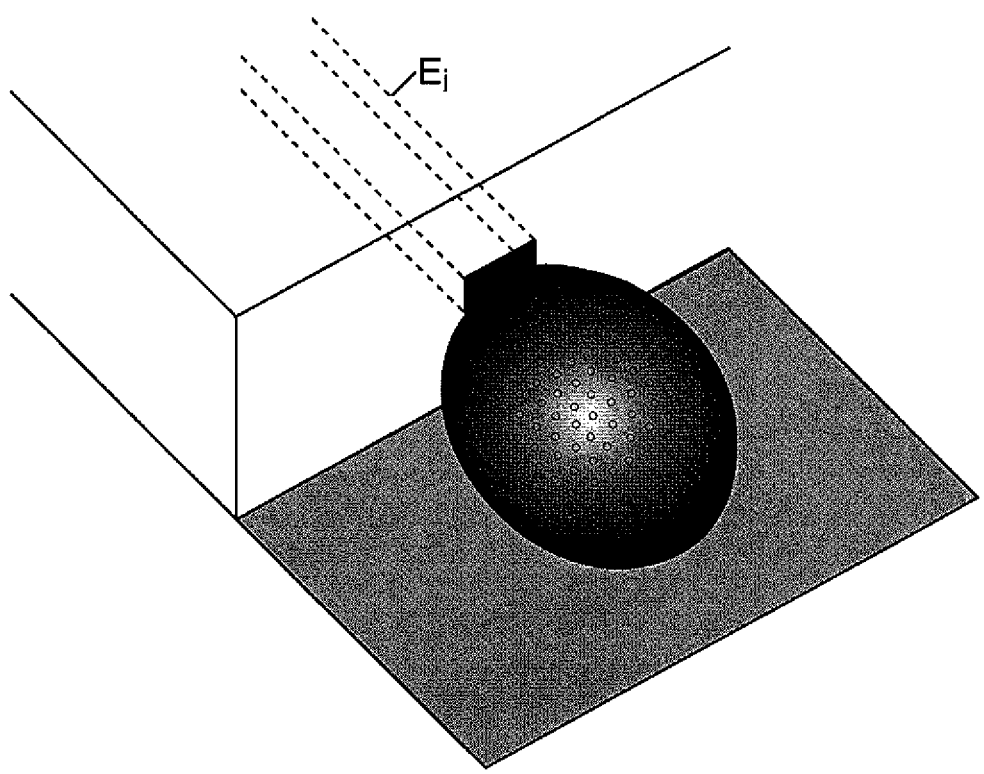
FIG. 6 is a schematic illustration how droplets can be generated at the chip interface; the liquid from the microchannel is continuously dispensed on a surface until a specific droplet volume is achieved.

For both schemes, after the analyte zones have been transferred into the extraction channels, an electric field is reapplied along the main separation channel, which varies in its length between 1 mm and 50 cm, to transport the remaining analyte molecules into the waste reservoir 13, 22 or 31. Then, the flow along the extraction channels is applied to fully transfer the analyte zones into the extraction reservoirs. This process allows reducing the entrance of contaminating molecules into the extraction channels. Instead of transporting the analytes into the extraction reservoirs, they can also be dispensed into droplets as shown in FIG. 6. For this step, liquid is continuously dispensed out of the abrupt ending microchannel on a surface until the desired droplet volume is achieved. Several droplets can be generated simultaneously through multiple extraction channels, and the droplets can be placed in a specific array for their subsequent analysis such as mass spectrometry, cryo-electron microscopy, AFM, infrared lasers, evanescent-field based technologies, surface-plasmon resonance imaging, or optical detections, for example.

In another embodiment, the extracted analytes can be reinjected according to FIG. 3 into an additional main separation channel where the analytes are preconcentrated and isolated further. Therewith, the analytes are purified sequentially wherein the first extraction module high abundant molecules are removed, and in the second extraction module selective isolation of the analytes is performed, for example. This can be achieved by using different ITP buffer systems (pH, ionic strength, effective electrophoretic mobility) for the first and second extraction module.

Figure 7A:
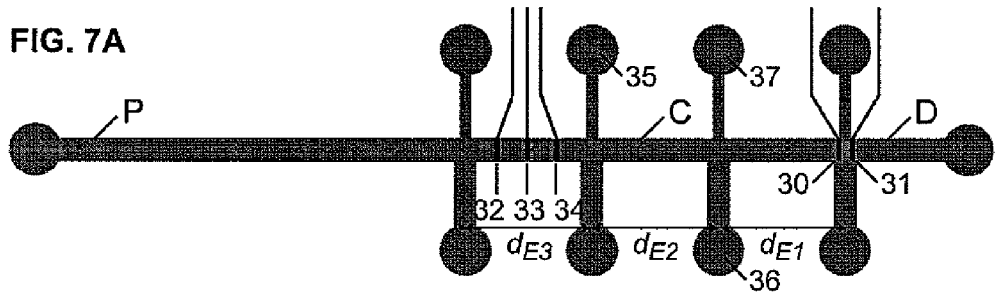
FIG. 7A is a schematic diagram of the detection electrodes in the main separation channel or reservoirs, which are used to control the ITP process.
Figure 7B:
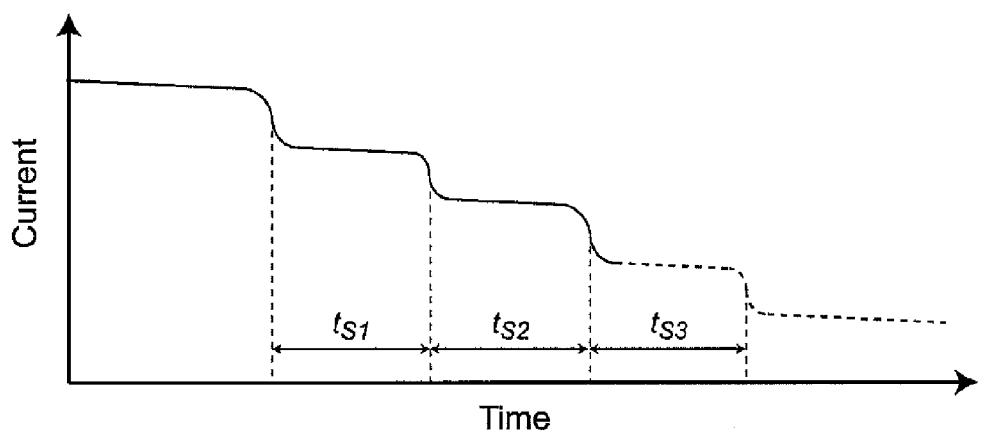
FIG. 7B shows the current measured with electrodes 30 and 31, 32 and 33, 33 and 34, 35 and 36, or 36 and 37 for the case n=4, once three spacers have passed these electrodes; analytes 1-4 are focused in peak mode ITP, not resulting in a constant current during their passage.
Figure 7C:
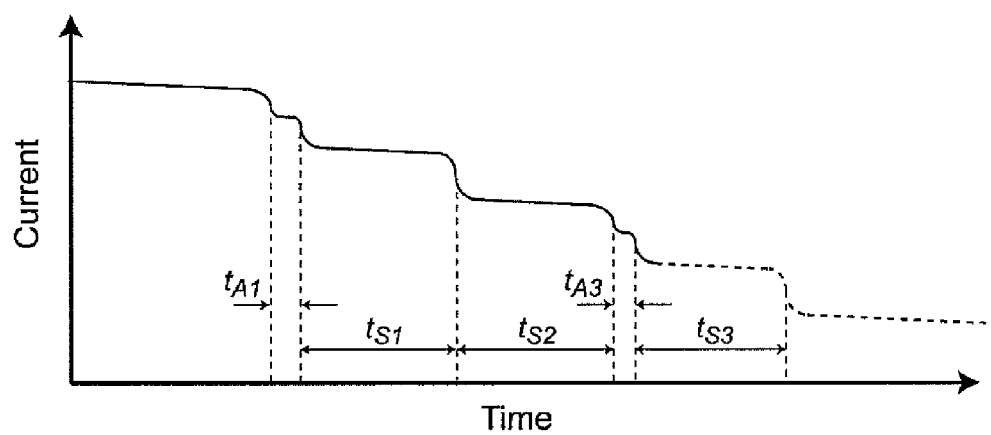
FIG. 7C equal as FIG. 7B, but analytes 1 and 3 are focused in plateau mode ITP, resulting in a detectable current plateau.

To stop the ITP focused zones once they are opposite to their extraction channels, the ITP process has to be monitored. Different detection methods can be applied such as electrical, electrochemical, fluorescence, thermo-optical absorbance, radiochemical, or UV absorbance detection, for example, and an electrical detection scheme is described here. The method can employ different numbers of electrodes as shown in FIG. 7, such as for example two electrodes to detect a change in the conductivity of the focused zone, or three electrodes to measure a change in the conductivity and calculate the velocity of the ITP zones. FIG. 7B shows the measured current once three spacer molecules have passed electrodes 30 and 31, 32 and 33, 33 and 34, 35 and 36, or 36 and 37. As shown in FIGS. 7A and B, $d_{Ek}$ is proportional to the time interval $t_{Sk}$ of the spacer compounds. FIG. 7B shows the electrical signal of a sample containing n=4 analytes which are focused in peak mode ITP, not resulting in a constant current during their passage. In contrast, analytes 1 and 3 are focused in plateau mode ITP in FIG. 7C, leading to a directly detectable current plateau during the time intervals $t_{A1}$ and $t_{A3}$. The two electrodes 30 and 31 are located just at the entrance of an extraction channel such that the ITP process can be switched off immediately upon arrival of the analytes of interest. Differently, three electrodes 32 to 34 can be located between the extraction channels to measure the velocity at which the analytes are migrating downstream, allowing to time the ITP electric field termination and the subsequent extraction process. Further, the electrodes can be placed directly in reservoirs 35 to 37 to detect conductance changes in the main separation channel.

Example

Separation and Extraction of Bovine Serum Albumin (BSA) and Concanavalin A (ConA)

BSA has numerous biochemical applications and many functions. It has been claimed that denatured ConA might reduce the probability of a person acquiring certain diseases, such as insulin dependent diabetes or auto-immune diseases. Due to the biochemical and biological significance of BSA and Concanavalin A, an ITP extraction assay is designed here.

For the selection of the buffer system we first specify the solution pH, for which step the isoelectric points 4.7 of BSA and 6.5 of ConA have to be considered. A physiological pH of 7.4 is chosen, such that BSA and ConA are negatively charged. Next, the effective electrophoretic mobility of BSA and ConA have to be measured, and we chose the second method described above by which the effective mobility of the TE is incrementally increased. For the LE an anion with a high effective electrophoretic mobility is chosen: hydrochloric acid (see Peakmaster's database). To adjust the pH to 7.4 the buffering counterion TRIS is selected, and to have a conductivity of ~0.8 S m$^{-1}$ as described above, this leads to the following concentrations (calculated with Peakmaster): 120 mM TRIS-100 mM HCl. The electro-osmotic flow is suppressed by the addition of 1% poly(n-vinylpyrrolidone) (PVP) MW 1,000,000 to the LE.

The TE has to have a low effective electrophoretic mobility, and TAPS is therefore selected from Peakmaster's database. For the buffering counterion TRIS is chosen, and to achieve a conductivity of ~0.03 S m$^{-1}$ as described above, the following concentrations are calculated with Peakmaster: 5 mM TRIS-20 mM TAPS (pH 7.6). For the determination of the effective electrophoretic mobility of BSA and ConA by the incremental effective mobility increase of the TE, BSA and ConA conjugated with Alexa Fluor 488 are used for fluorescent investigations and added to the TE at tens to hundreds of nM, respectively. All chemicals were bought from Sigma-Aldrich, except PVP was from Polysciences, and the fluorescent proteins BSA and ConA were bought from Invitrogen.

The measurements were performed on an inverted fluorescence microscope Nikon Eclipse TE300, equipped with a 100 W mercury lamp, a 10× Plan Fluor objective (NA 0.3), and a green filter cube (465-496 nm excitation, 515-555 nm emission, 505 nm cutoff dichroic). Images were captured with the Moticam 2300 controlled with the software Motic Life.

Microfluidic chips with two extraction channels $E_1$ and $E_2$ were used, and the protocol of FIG. 4 was applied. The microchannels were 20 µm deep and 30 to 80 µm wide. For the generation of a pressure-driven flow for the filling or solution exchange procedure, a vacuum pump was used. The voltage was generated with a DC/DC converter G60R from EMCO High Voltage Corporation, controlled with the data acquisition tool USB-6008 from National Instruments and the software Matlab from MathWorks. The resulting electric field of ~100 V cm$^{-1}$ was applied with platinum electrodes which were inserted into the reservoirs.

Figure 8A:
FIGS. 8A to C are fluorescence images of BSA and ConA focusing between the described LE, TE and spacer.
Figure 8B:
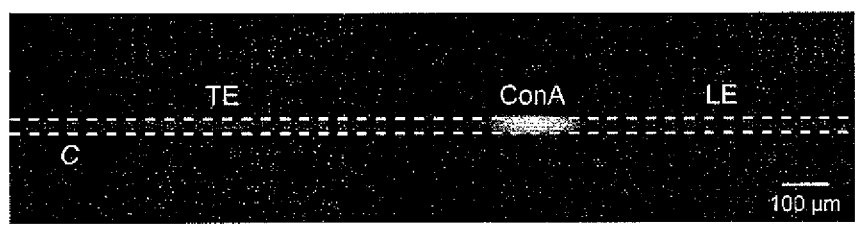

Experiments are first performed with BSA to measure its effective electrophoretic mobility, and the LE and TE are used as previously described. BSA is focusing with the electrolyte system TRIS-HCl and TRIS-TAPS, and the effective mobility of the TE is therefore increased. A new TE with a higher effective mobility according to Peakmaster's database is prepared: 9 mM TRIS-15 mM HEPES (pH 7.4). As shown in FIG. 8A, BSA is still preconcentrating by ITP and the TE effective mobility is increased again. With 12 mM TRIS-10 mM caproic acid focusing is no longer observed and the effective electrophoretic mobility of BSA is thus between the one of caproic acid and HEPES at approximately $-23 \times 10^{-9}$ m$^2$ V$^{-1}$ s$^{-1}$. Next, ConA is investigated and the same procedure as for BSA is applied. ConA is preconcentrating with TRIS-TAPS (FIG. 8B) but not with TRIS-HEPES, and the effective electrophoretic mobility of BSA is therefore estimated to be at approximately $-7.5 \times 10^{-9}$ m$^2$ V$^{-1}$ s$^{-1}$.

Figure 8C:
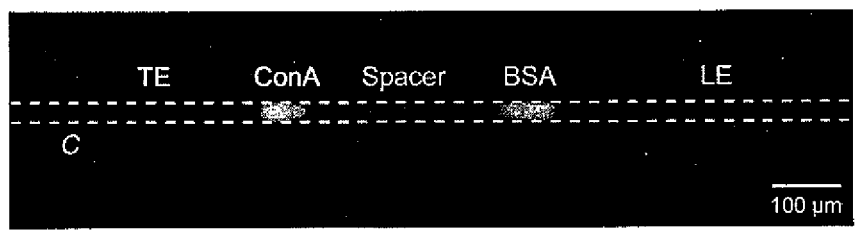

Based on these results, the TE with the spacer for the separation of BSA and ConA is designed. Since ConA is focusing with TAPS and BSA with HEPES, the following TE is designed with Peakmaster: 5 mM TRIS-20 mM TAPS-70 µM HEPES (pH 7.6). The concentration of HEPES is chosen such that the separation distance between BSA and ConA corresponds to the inter-channel separation distance $d_{E1}$ of 600 µm according to EQ. (5). FIG. 8C shows the simultaneous focusing and separation of these two fluorescent proteins.

Figure 8D:
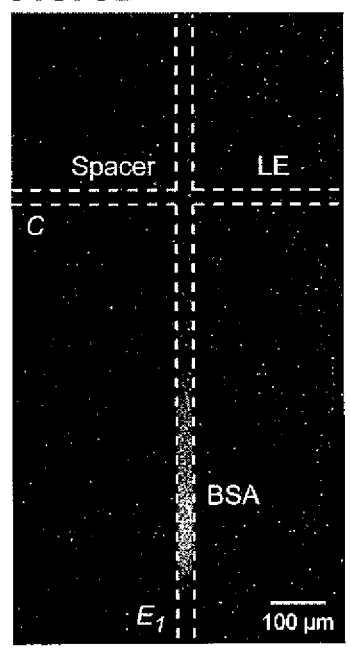
FIG. 8D shows the extraction of BSA in the extraction channel $E_1$, and ConA is preconcentrated further upstream between the spacer and TE (not illustrated).

To transfer the proteins into the extraction channels, the ITP process is stopped upon arrival of the focused zones at the corresponding ITP channel—extraction channel crossings. Then, an electric field is applied along the entire length of the extraction channels such that BSA and ConA are transported into the extraction channels as shown in FIG. 8D for BSA. This extraction step is terminated once the proteins arrive in the extraction reservoirs. To increase the extraction purity a different protocol can be used, by which the electric field is switched off immediately after the biomolecules have been completely transferred into the extraction channels. Then, the ITP electric field is reapplied until the main separation channel is free of analytes, and only then the flow along the extraction channels is reapplied to fully transfer the biomolecule zones into the extraction reservoirs.

The invention claimed is:

1. A method for preconcentrating and isolating a plurality n of charged analytes ($A_i$, with i=1 to n) contained in a sample by isotachophoresis, each one of said analytes $A_i$ having an effective electrophoretic mobility $\mu_{Ai}$, said effective electrophoretic mobilities $\mu_{Ai}$ obeying the fully ordered relationship $\mu_{A1} > \mu_{A2} >$ etc. $> \mu_{An}$, by means of an apparatus comprising:
   a main separation channel (C) with a proximal end (P) and a distal end (D),
   means for loading a supplemented sample portion into an internal segment of said main separation channel located between said proximal end and said distal end,
   means for applying an electric field ($\hat{E}$) between said proximal end (P) and said distal end (D),
   a plurality n of extraction channels ($E_i$, with i=1 to n) being transversely oriented in respect of said main separation channel (C) and having respective junctions with said main separation channel located at different sites thereof, each extraction channel having an extraction part leading out of the main separation channel,
   means for detecting focused zones within said separation channel (C) and/or means for measuring a flow velocity along a longitudinal axis of said separation channel under the influence of an electric field ($\hat{E}$) applied along said axis by said means for applying an electric field,
   means for applying a transversal flow along each one of said extraction channels ($E_i$) for extracting any one of said analytes located at the respective junction of the extraction channel ($E_i$) and the main separation channel (C),
said method comprising the steps of:
   loading a leading electrolyte (LE) into a distal channel region adjacent said distal end and a trailing electrolyte (TE) into a proximal channel region adjacent said proximal end, said leading electrolyte (LE) having an effective electrophoretic mobility $\mu_{LE} > \mu_{A1}$ and said trailing electrolyte (TE) having an effective electrophoretic mobility $\mu_{TE} < \mu_{An}$,
   adding a supplemented sample to said proximal channel region (P),
   said supplemented sample comprising a mixture of said sample and a number n−1 of spacer compounds ($S_k$, with k=1 to n−1), each one of said spacer compounds ($S_k$) having an effective electrophoretic mobility $\mu_{Sk}$, said effective electrophoretic mobilities $\mu_{Sk}$ obeying the fully ordered relationship $\mu_{Ak} > \mu_{Sk} > \mu_{Ak+1}$, applying an axial electric field between said proximal end (P) and said distal end (D), thereby causing a preconcentration and separation of said analytes and spacers forming respective focused spacer zones and focused analyte zones that flow along said longitudinal axis, each one of said spacer compounds ($S_k$) in said supplemented sample having an initial concentration ($c_{0,Sk}$) selected in such manner as to substantially correspond, at its preconcentrated concentration ($c_{Sk}$) in the respective focused spacer zone, to a volume of said main separation channel enclosed between an associated pair of adjacent extraction channels ($E_k$) and ($E_{k+1}$), detecting the position and/or measuring the velocity of said focused zones, optionally stopping the process by switching off said electric field ($\hat{E}$) when the focused zone of each analyte ($A_i$) is located at the respective junction with the extraction channel ($E_i$), applying a transversal flow of the part of the supplemented sample located at the junction of the main separation channel and the respective extraction channel, thereby transferring each preconcentrated analyte ($A_i$) away from the main separation channel for said analyte isolation.

2. The method according to claim 1, wherein said adding a supplemented sample to the proximal channel region comprises loading said supplemented sample into a channel segment between said leading electrolyte (LE) and said trailing electrolyte (TE).

3. The method according to claim 1, wherein said adding a supplemented sample to the proximal channel region comprises loading a mixture of said supplemented sample and said trailing electrolyte into said proximal channel region.

4. The method according to claim 1, wherein the presence of an analyte ($A_i$) and optionally the instant concentration thereof is detected electrically as a current or resistance plateau between:

two adjacent spacer compounds ($S_{i-1}$) and ($S_i$) for i=2 to n−1;

the leading electrolyte (LE) and adjacent spacer compound ($S_1$) for $A_1$;

adjacent spacer compound ($S_{n-1}$) and the trailing electrolyte (TE) for $A_n$.

5. The method according to claim 1, wherein said step of applying a transversal flow is carried out until each analyte ($A_i$) has reached a collection zone located at an end of the extraction part of the respective extraction channel ($E_i$).

6. The method according to claim 1, wherein said step of applying a transversal flow is interrupted when each analyte ($A_i$) has accumulated in a zone of the respective extraction channel ($E_i$) displaced from said main separation channel (C), followed by a step of reapplying said electric field ($\hat{E}$) and thus causing any residual analyte present in the main separation channel (C) to be removed therefrom towards said distal end (D), followed by switching off said electric field ($\hat{E}$) and reapplying said transversal flow until each analyte ($A_i$) has reached a collection zone located at an end of the extraction part of the respective extraction channel ($E_i$).

7. The method according to claim 1, wherein the leading electrolyte (LE) and the trailing electrolyte (TE) have substantially the same pH value, and optionally contain a sieving matrix and an agent for electro-osmotic flow suppression.

8. The method according to claim 1, wherein the effective electrophoretic mobility ($\mu_{Ai}$) of a given analyte ($A_i$) is determined by means of isotachophoresis or electrophoresis.

9. The method according to claim 1, wherein the step of selecting the initial concentration ($c_{0,Sk}$) of each one of said spacer compounds ($S_k$) comprises the steps of:

a) providing a mixture of said spacer compounds ($S_k$) with respective startup initial concentrations ($c'_{0,Sk}$), b) starting an isotachophoretic process with said mixture, thereby causing a separation and preconcentration of said spacer zones flowing along said longitudinal axis, c) determining the associated length ($d_{Sk}$) of each spacer zone, d) determining a deviation measure ($m_k$) for each one of said lengths ($d_{Sk}$) versus the distance ($d_{Ek}$) between the associated pair of adjacent extraction channels ($E_k$) and ($E_{k+1}$), e) using said deviation measures ($m_k$) to calculate a set of refined initial concentrations ($c''^{(r)}_{0,Sk}$), f) repeating steps a) to e) using said refined initial concentrations ($C''^{(r)}_{0,Sk}$) instead of said startup initial concentrations ($c'_{0,Sk}$) until none of said deviation measures ($m_k$) exceeds a predefined tolerance threshold, g) using said refined initial concentrations ($c''^{(r)}_{0,Sk}$) as the initial concentrations ($c_{0,Sk}$) for preparing said supplemented sample.

10. The method according to claim 9, wherein said step a) includes adding said charged analytes ($A_i$) to said mixture and wherein said step of determining the associated length ($d_{Sk}$) of each spacer zone is carried out by detecting focused analyte zones separating said focused spacer zones.

* * * * *